US007667057B2

(12) United States Patent
Regiert et al.

(10) Patent No.: US 7,667,057 B2
(45) Date of Patent: Feb. 23, 2010

(54) COSMETIC COMPOSITION COMPRISING A COMPLEX OF CYCLODEXTRIN AND VITAMIN F

(75) Inventors: Marlies Regiert, München (DE); Michaela Kupka, Burghausen (DE)

(73) Assignee: Wacker-Chemie GmbH, Munich (DE)

( * ) Notice: Subject to any disclaimer, the term of this patent is extended or adjusted under 35 U.S.C. 154(b) by 396 days.

(21) Appl. No.: 10/712,703

(22) Filed: Nov. 12, 2003

(65) Prior Publication Data
US 2004/0096413 A1 May 20, 2004

(30) Foreign Application Priority Data
Nov. 14, 2002 (DE) .............................. 102 53 042

(51) Int. Cl.
*A61K 31/724* (2006.01)
*C08B 37/16* (2006.01)
*C07C 57/03* (2006.01)
*C07C 57/12* (2006.01)

(52) U.S. Cl. .................. 554/3; 554/223; 554/224; 514/23; 514/54; 514/58; 536/123.12; 536/103; 536/560

(58) Field of Classification Search ............... 424/59, 424/401, 489; 514/27, 183
See application file for complete search history.

(56) References Cited

U.S. PATENT DOCUMENTS

| | | | | |
|---|---|---|---|---|
| 4,393,043 A * | 7/1983 | Koulbanis et al. | ............ | 424/59 |
| 4,438,106 A * | 3/1984 | Wagu et al. | ................ | 514/58 |
| 4,559,225 A * | 12/1985 | Fourman | .................... | 424/59 |
| 4,732,759 A | 3/1988 | Shibanai et al. | | |
| 4,775,749 A | 10/1988 | Hijiya et al. | | |
| 5,250,289 A * | 10/1993 | Boothroyd et al. | ........... | 424/59 |
| 5,690,948 A * | 11/1997 | McCook et al. | ............ | 424/401 |
| 5,710,177 A * | 1/1998 | Sauermann et al. | ......... | 514/557 |
| 6,025,510 A | 2/2000 | Wimmer et al. | | |
| 6,224,888 B1* | 5/2001 | Vatter et al. | ................ | 424/401 |
| 6,284,281 B1* | 9/2001 | Chevalier et al. | .......... | 424/489 |
| 6,638,557 B2* | 10/2003 | Qi et al. | ...................... | 426/601 |
| 6,649,178 B2* | 11/2003 | Mohammadi et al. | ....... | 424/401 |
| 6,811,770 B2* | 11/2004 | Ferrari et al. | ............... | 424/64 |
| 6,908,625 B2* | 6/2005 | Lee et al. | .................... | 424/450 |
| 7,074,419 B2* | 7/2006 | Dietz et al. | ................ | 424/401 |
| 2003/0228267 A1* | 12/2003 | Aust et al. | .................... | 424/59 |
| 2004/0067894 A1* | 4/2004 | Carola et al. | ................ | 514/27 |

FOREIGN PATENT DOCUMENTS

| | | |
|---|---|---|
| CH | 646049 | 11/1984 |
| CH | 689373 | 3/1999 |
| DE | 19612658 | 10/1997 |
| EP | 0470452 | 2/1992 |
| EP | 1041136 | 10/2000 |
| JP | 60-181014 | 9/1985 |
| JP | 11-506496 A | 6/1999 |
| WO | 9709039 | 3/1997 |
| WO | 97/36972 | 10/1997 |
| WO | WO-00/53637 | 9/2000 |
| WO | WO0222100 A1 * | 3/2002 |
| WO | 0238123 | 5/2002 |

OTHER PUBLICATIONS

GE Silicones Catalog; Silicone Specialities For Personal Care; 2001.*
Lohman et. al. Nexbase Polydecenes; New Safe, Soft and Sophisticated Ingredients for Cosmetics Formulations: 2001.*
Wacker Silicones: Wacker-Belsil SPG 128 VP.*
Schlenk et. al., J. Am. Chem. Soc., 83, 2312-2320, 1961.*
Wu et. al., The Journal of Nutrition, 2001, 72-79.*
Cunnane et. al. Progress in Lipid Research, 42, 2003, 544-568.*
Schlenk et al., "Stabilization of Autoxidizable Materials by Means of Inclusion" Journal of the American Chemical Society (1955) vol. 77. pp. 3587-3590.*
Reichenbach et al., "Oxidative Stability and Nuclear Magnetic Resonance Analyses of Linoleic Acid Encapsulated in Cyclodextrins" Journal of the American Oil Chemists Society (1997) vol. 74 No. 10, pp. 1329-1333.*
Wacker Silicones: Wacker-Belsil SPG 128 VP, published Aug. 29, 2003.*
Szente et al. "Fatty Acid-Cyclodextrin Complexes: Properties and Applications"; Journal of Inclusion Phenomena and Molecular Recognition in Chemistry, vol. 16, 1993, pp. 339-354.
English Derwent Abstract AN 1994-220438 [11] corresp. to JP 06 153860.
English Derwent Abstract AN 199541 corresp. to JP 07215911.
English Derwent Abstract AN 1999-205411 [18] corresp. to CH 689373.
Landaus: "International Dictionnary of Medicine and Biology", 1986, John Wiley & Sons, USA vol. III, p. 3159.
English Derwent Abstract AN 1997-481763 [45] corresp. to DE 196 12 658 A1.
English Derwent Abstract AN 1981-56976D [32] corresp. to CH 646049.
English Derwent Abstract AN 1985-267433 [43] corresp. to JP 60 - 181014.
Simo Laakso, Biol. Food Chem. Aspects, Contrib. Lipid forum/Sik Symp., Meeting Date 1985, pp. 165-170.
López-Nicolás, et al; Cinoleic acidcyc lodextrin inclusion complexes in aqueous solutions, Biochem. J. (1995), vol. 308, pp. 151-154.
US 6,025,510 is corresponding to JP 11-506496, Issued Feb. 15, 2009.

* cited by examiner

*Primary Examiner*—Shaojia Anna Jiang
*Assistant Examiner*—Eric S Olson
(74) *Attorney, Agent, or Firm*—Collard & Roe, P.C.

(57) ABSTRACT

Cosmetic or dermatological preparations are based upon vitamin F, and the vitamin F is present in the form of a complex with a cyclodextrin which includes alpha-cylodextrin, beta-cyclodextrin, and gamma-cyclodextrin.

5 Claims, 1 Drawing Sheet

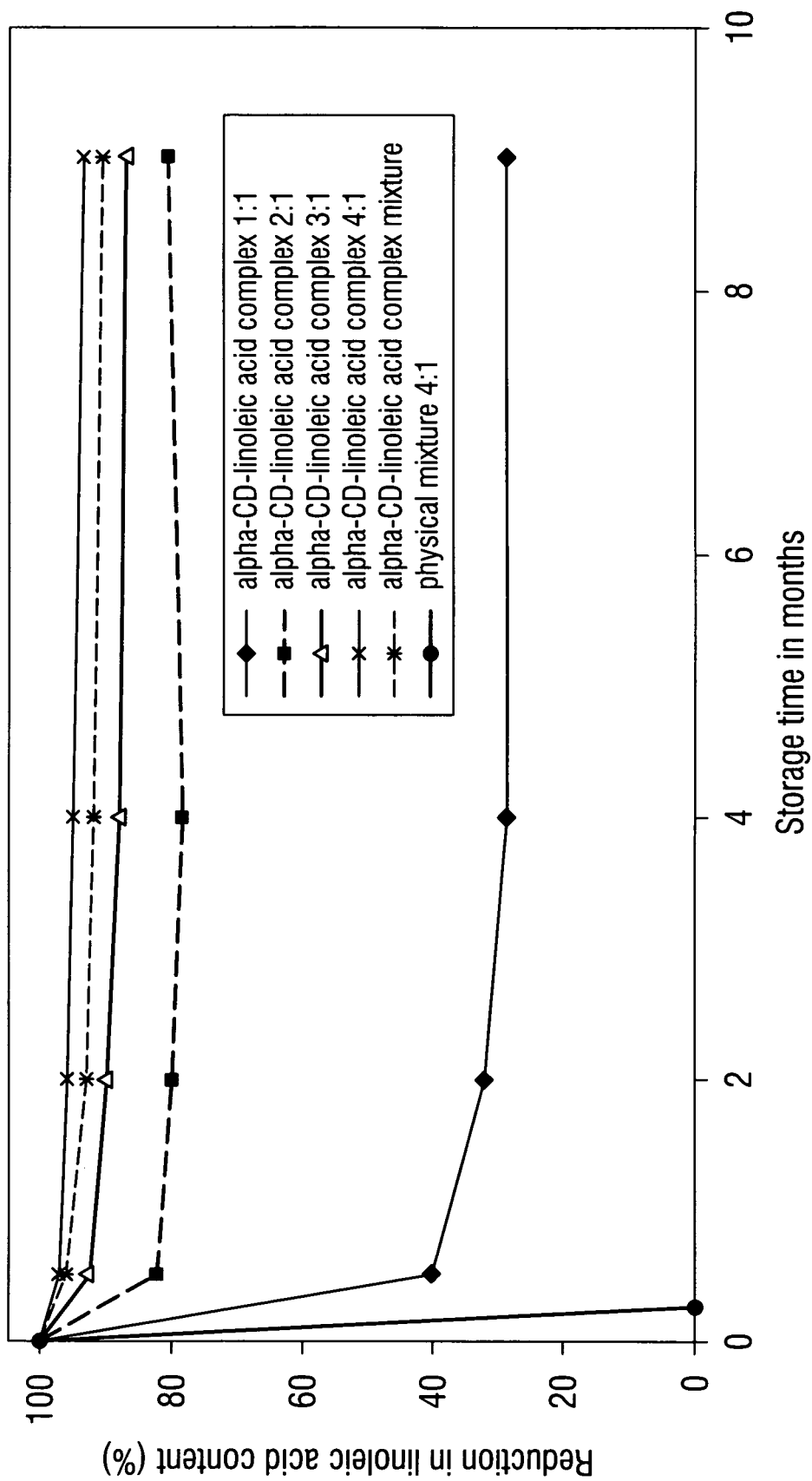

COSMETIC COMPOSITION COMPRISING A COMPLEX OF CYCLODEXTRIN AND VITAMIN F

BACKGROUND OF THE INVENTION

1. Field of the Invention

The invention relates to a cosmetic preparation comprising a complex of cyclodextrin and vitamin F, and to preferred complexes of cyclodextrins and vitamin F.

2. The Prior Art

Cyclodextrins are cyclic oligosaccharides which are built up from 6,7 or 8 α(1-4)-linked anhydroglucose units. The α-, β- or γ-cyclodextrins produced by enzymatic starch conversion differ in the diameter of their hydrophobic cavity and are generally suitable for the inclusion of numerous lipophilic substances.

Vitamin F consists essentially of a mixture of essential fatty acids (EFA), in particular omega-6-polyunsaturated fatty acids. Therefore, for the purposes of the present invention, vitamin F is preferably understood as meaning EFA, in particular omega-6-polyunsaturated fatty acid. The body is unable to produce EFA by itself in the required amount; however, an adequate supply is essential for natural functions of the body. The expression "essential fatty acids" used in the present application includes preferably unsaturated fatty acids with chain lengths greater than or equal to 18 carbon atoms which have at least two double bonds. The omega-6-polyunsaturated fatty acids are particularly preferably linoleic acid and its isomers, linolenic acid and its isomers, and other acids which are very sensitive to oxidation. As has been found, vitamin F develops certain properties which are particularly desirable, inter alia, for improving the appearance of the skin.

In investigations, it was in particular found that combinations of at least one essential fatty acid or mixtures thereof and in particular of vitamin F have a notable stability toward oxidation which is not found when essential fatty acids and, in particular, vitamin F are not used in the form of the active ingredient combination according to the invention.

The topical application of vitamins in cosmetics has already been proposed by a number of authors. Vitamins which have been particularly recommended which may be mentioned are vitamin A, vitamin B, vitamins $B_2$, and $B_6$, vitamin E, vitamin H and cyclodextrin complexes thereof, and certain suitable vitamin mixtures, such as a mixture of vitamin A, vitamin E and vitamin $D_3$, which combination has a synergistic effect.

The vitamin which is of particular interest to the formulators of cosmetic products is vitamin F. It exerts a favorable effect on dry and rough skin, and on skin which exhibits particular symptoms of irritation. The use of vitamin F in cosmetics has always been impaired by the particularly acute problem which is essentially regarded as being the great instability of this material toward oxidation by the oxygen in the atmosphere. In particular, it has been found that very rapidly after storage or first use, decomposition products with a rancid odor form which prevent further use of cosmetic preparations based on this vitamin. Since vitamin F consists essentially of linoleic acid and its isomers and, in particular, linolenic acid and its isomers and other acids which are very sensitive toward oxidation, the corresponding alcohols or the esters, e.g. the triglycerides, of this acid have preferentially been used in cosmetics and in foodstuffs. These are more stable, although in this a case a considerable loss in activity has to be accepted. Possible ways of stabilizing the essential fatty acids are thus of extraordinary interest.

The expression "essential fatty acids" used in the present application particularly preferably includes unsaturated fatty acids which have at least two double bonds, such as:

linoleic acid or 9,12-octadecadienoic acid of the formula

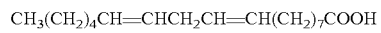

and stereoisomers thereof, in particular the z-9, z-12 isomers, and positional isomers thereof or conjugated linoleic acids, i.e.:

9,11-octadecadienoic acid of the formula

and stereoisomers thereof;

10,12 octadecadienoic acid of the formula

and stereoisomers thereof;

α-linolenic acid or 9,12,15-octadecatrienoic acid of the formula

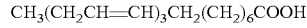

and stereoisomers thereof and in particular the z-9, z-12, z-15 isomer;

γ-linolenic acid or 6,9,12-octadecatrienoic acid of the formula

and stereoisomers thereof; and arachidonic acid or 5,8,11,14-eicosatetraenoic acid of the formula

Important physiological functions of vitamin F, inter alia due to the high content of linoleic acid, are the formation of arachidonic acid, a constituent of phospholipids (cell membranes) and prostaglandins (autocoids), which have an influence on the serum cholesterol level and the blood pressure. A lack of linoleic acid leads, in children, to growth disorders, increased susceptibility to infection, skin changes (eczema) and to impaired function of the capillaries. Vitamin F is used in wound healing disorders. The skincare properties which are to be found even for a low concentration make it an extremely valuable substance. In the field of cosmetics, therefore, there is great interest in the increased use of vitamin F, particularly in dermatological formulations. The topical application of vitamin F stabilizes the balance of fatty acids in the skin. A deficiency of vitamin F leads to damage specifically of the cell membranes of the skin (phospholipid structure) and also in the skin lipids (ceramide structure) to increased wrinkling and keratinization ("photoaging") and to a loss in skin elasticity. The skin lipids with a high content of polyunsaturated fatty acids, such as linoleic acid, exhibit a relatively high packing density, which evidently strengthens the barrier function against microorganisms, and also reduced transepidermal water loss. This was proven in experiments on human and animal skin during topical application. In addition, skin lipids are synthesized from linoleic acid.

The main problem preventing more widespread use of vitamin F is its sensitivity toward oxidation, in particular under exposure to light.

An autoxidation takes place at the conjugated unsaturated hydrocarbon chain of the fatty acid molecule, leading to the formation of numerous decomposition products, to isomerizations and polymerizations. When fats become rancid, the linoleic acid, one of the essential fatty acids, can, for example, convert to an isomeric fatty acid with conjugated double bond, which no longer has vitamin character and may even increase deficiency damage. A viscous-liquid mass is formed from the originally oily, thin-liquid substance. The odor is perceived as intensively rancid. As a result of intermediately formed peroxides, the toxic potential of the formulations increases, the cosmetically and nutritional-physiologically desired effect of the intact vitamin F is reduced.

As stated above, vitamin F consists essentially of linoleic acid and isomers thereof, where, particularly preferably, the 9,12-isomer is present in an amount between about 40% and 70%, where the total content of the linoleic acid and isomers thereof forms about 80% to 90% of the material. The remainder of the material consists essentially of a mixture of other essential fatty acids.

CH 646049 describes the preparation of oxidation-resistant cosmetic preparations which comprise vitamin F or essential fatty acids by means of a vegetable oil, namely jojoba oil.

Biol. Food Chem. Aspects, Contrib. Lipid forum/Sik Symp., Meeting Date 1985, 165-70 describes the stabilization of lipids via the molecular inclusion of linoleic acid with cyclodextrins with caseine as antioxidant in dispersion.

Biochem. J. (1995) 308, 151-154 (printed in Great Britain) discloses the use of "soluble lipids" for biochemical processes by means of linoleic acid-CD complexes in aqueous solution.

Japanese patent specification 60181014A describes the preparation of bathing product additives containing vitamins, inter alia vitamin F, by means of cyclodextrins and diastase.

SUMMARY OF THE INVENTION

It is an object of the present invention to provide a cosmetic or dermatological preparation comprising vitamin F which is stabilized against oxidative decomposition.

This object is achieved according to the present invention by a preparation wherein the vitamin F is present in the form of a complex with a cyclodextrin selected from the group consisting of alpha-cyclodextrin, beta-cyclodextrin, and gamma-cyclodextrin.

The cosmetic or dermatological preparation according to the invention is oxidation-resistant and is preferably suitable for the care and protection of the skin, in particular of sensitive and of dry skin. In particular, it repairs damage associated with skin aging and serves for prophylaxis, in a lasting manner and without the risk of secondary effects, by avoiding the disadvantages of the prior art.

The complex of vitamin F and cyclodextrin (CD) can be prepared here in a manner known per se from, for example, solution or using a paste method. The preparation from concentrated, aqueous CD solutions has proven to be advantageous. The CD concentration of the aqueous solutions is preferably between 5-50% by weight, preference being given to a CD concentration of 20-50% by weight. The CD concentration percent by weight is based upon the total weight of the aqueous solution.

The weight ratio of vitamin F to CD is between 1:4 and 1:40, preferably between 1:15 and 1:20. The batches are intensively stirred or kneaded depending on consistency.

The reaction temperature is usually 20-85° C. Preference is given to working at 20-75° C., particularly preferably at 50-70° C. The reaction time depends on the temperature and is preferably between an hour and several days. Preference is given to a reaction time of from 30 to 80 hours.

The complexation usually takes place under atmospheric pressure. Preferably, the complexation takes place under a protective-gas atmosphere (nitrogen or argon).

The sparingly water-soluble complexes of vitamin F and CD can be used directly. They can, however, also be isolated and worked up in an appropriate manner by filtration, centrifugation, drying, grinding, sieving, screening, granulation, tableting. Particularly advantageous complexes of cyclodextrin and at least one fatty acid of vitamin F or essential fatty acid are those which have the following molar ratios:

1 mol of alpha-cyclodextrin:1 mol of an essential fatty acid 2 mol of alpha-cyclodextrin:1 mol of an essential fatty acid 3 mol of alpha-cyclodextrin:1 mol of an essential fatty acid 4 mol of alpha-cyclodextrin:1 mol of an essential fatty acid 1 mol of beta-cyclodextrin:1 mol of an essential fatty acid 2 mol of beta-cyclodextrin:1 mol of an essential fatty acid 3 mol of beta-cyclodextrin:1 mol of an essential fatty acid 1 mol of gamma-cyclodextrin:1 mol of an essential fatty acid 2 mol of gamma-cyclodextrin:1 mol of an essential fatty acid 3 mol of gamma-cyclodextrin:1 mol of an essential fatty acid and a mixture of these complexes.

Particular preference is given to complexes of alpha-, beta- or gamma-cyclodextrin and an essential fatty acid in the molar ratio 3:1 or 4:1, and to a mixture comprising these complexes.

In the investigations relating to the present invention it has been found that these complexes in particular stabilize vitamin F to a particularly high degree. (FIG. 1)

The present invention therefore also relates to complexes of cyclodextrin and an essential fatty acid in the molar ratio 3:1 or 4:1, and to a mixture comprising these complexes. The cyclodextrin is particularly preferably alpha-cyclodextrin.

Preferably, the mixture comprises 4:1 molar complexes of alpha CD and essential fatty acid in an amount of from 10% to 90% by weight, 3:1 molar complexes of alpha CD and essential fatty acid in an amount of from 40% to 80% by weight, 2:1 molar complexes of alpha CD and essential fatty acid in an amount of from 30% to 70% by weight, 1:1 molar complexes of alpha CD and essential fatty acid in an amount of from 20% to 60% by weight. The percent by weight of the complex is based upon the total weight of the mixture.

The cosmetic and dermatological formulations which comprise the active ingredient combination of cyclodextrin with vitamin F, preferably an essential fatty acid, are in various forms, e.g. emulsions of the water-in-oil (W/O) or oil-in-water (O/W) type, preparations of this type are milk preparations, lotions, creams or ointments, and gels, powders, masks, packs, sprays, aerosols or sticks, which are used either to color the lips or to treat chapped lips, or make-up products for the eyes or face make-up.

A complex according to the invention or a mixture of the complexes according to the invention can also be applied to textiles or nonwovens and thereby be provided to the skin via this medium.

Cosmetic and dermatological formulations according to the invention preferably also comprise linear and cyclic silicone oils, e.g. dimethicones and cyclomethicones, humectant agents, i.e. substances which protect the skin from drying out, such as propylene glycol, Mg sulfate, glycerol, substances which care for the skin, such as cetyl alcohol, liquid paraffin, petrolatum, caprylic/capric triglycerides, mineral oils, stearic acid, beeswax, candelilla wax, isopropyl and myristyl myristates, octyldodecanol, octyldodecyl lanolates, polyethylene glycol (PEG)-22/dodecyl glycol copolymer, hydrolyzed wheatgerm protein, natural oils, e.g. sunflower oil, soybean oil, almond oil, palm oil, coconut oil and olive oil gel formers, such as salts of carbopol, polymethacrylates, polysaccharides O/W and W/O emulsifiers, e.g.: polysorbate 20, PEG-40 stearate, PEG hydrogenated castor oil, aluminum, octyl or glyceryl stearates, lecithin, preservatives, such as urea, chlorhexidine digluconate, phenoxyethanol, sodium benzoate, sorbic acid, methyl-, ethyl-, butylparabens, BHT, BHA, bactericides, antioxidants like vitamin C and corresponding derivatives, alpha-hydroxy acids and corresponding derivatives, vitamin E and corresponding derivatives, sunscreen filters, such as UVA and UVB filters, e.g. oxygen 4-methylbenzylidenecamphor, DEA methoxycinnamates, benzophenone-4, octyldimethyl PABA, inorganic pigments, such as oxides of titanium, iron, zinc, self-tanning agents, such as: dihydroxyacetone, additives and auxiliaries, for example insect repellents, consistency-imparting agents, fillers, electrolytes, vitamins, alcohol, water, salts, stabilizers, dyes, perfumes, essential oils.

A composition according to the invention is prepared by incorporating a CD/vitamin F complex into a customary cosmetic or dermatological formulation. Preferably, the preparation takes place by dispersing the complex in water, and mixing the aqueous dispersion into the lipophilic part of the emulsion. This process step is essential for the cosmetic quality of the emulsion. Skincare products are characterized, when applied to the skin, by a pleasant feel on the skin. If the complexes are used in cosmetic emulsions without prior dispersion, a sandy to scratchy feel on the skin results during application. If the complex is not prepared in the manner described by dispersion to particle sizes of <200 micrometers, an additional processing step such as grinding or sieving is necessary. As a result of the dispersion, complexes of any particle size, i.e. including granules, can be used without additional comminution of large complex particles in cosmetic formulations such as emulsions. The dispersion can take place over a period of from 10 minutes to 2 hours at a temperature of from 20° C. to 80° C., preferably 30 minutes at 30-50° C.

BRIEF DESCRIPTION OF THE DRAWINGS

Other objects and features of the present invention will become apparent from the following detailed description considered in connection with the accompanying drawing which disclose several embodiments of the present invention. It should be understood, however, that the drawing is designed for the purpose of illustration only and not as a definition of the limits of the invention in which FIG. 1 shows the linoleic acid content in the stored samples as a function of the storage time.

DETAILED DESCRIPTION OF THE PREFERRED EMBODIMENTS

Example 1

Complexation of Linoleic Acid with α-Cyclodextrin a.) 100 g of $H_2O$ were added to 0.1 mol of α-cyclodextrin, 0.1 mol of linoleic acid were added, the mixture was homogenized and stirred for 30 h at RT, and for 8 h at 70° C. The active ingredient combination is dispersed in water, filtered, washed with water and dried at 40° C. under reduced pressure.

b.) 100 g of $H_2O$ were added to 0.1 mol of α-cyclodextrin, 0.05 mol of linoleic acid were added, the mixture was homogenized and stirred for 30 h at RT, and for 8 h at 70° C. The active ingredient combination is dispersed in water, filtered, washed with water and dried at 40° C. under reduced pressure.

c.) 100 g of $H_2O$ were added to 0.1 mol of α-cyclodextrin, 0.033 mol of linoleic acid were added, and the mixture was homogenized and stirred for 70 h at RT, and for 8 h at 70° C. The active ingredient combination is dispersed in water, filtered, washed with water and dried at 40° C. under reduced pressure.

d.) 100 g of $H_2O$ were added to 0.1 mol of α-cyclodextrin, 0.025 mol of linoleic acid were added, and the mixture was homogenized and stirred for 70 h at RT, and for 8 h at 70° C. The active ingredient combination is dispersed in water, filtered, washed with water and dried at 40° C. under reduced pressure.

Example 2

Preparation of the Physical Mixture α-Cyclodextrin/Linoleic Acid 4:1 (Comparative Example)

0.01 mol of α-cyclodextrin was weighed into a mortar and intensively triturated with 0.0025 mol of linoleic acid until a homogeneous powder was obtained.

Example 3

Determination of the Storage Stability of Complexes of α-Cyclodextrins and Linoleic Acid, and as Physical Mixture, Corresponding to a 4:1 Complex of α-Cyclodextrin with Linoleic Acid stored at 45° C.

Complex of α-cyclodextrins and linoleic acid 1:1

Complex of α-cyclodextrins and linoleic acid 2:1

Complex of α-cyclodextrins and linoleic acid 3:1

Complex of α-cyclodextrins and linoleic acid 4:1

Mixture of the active ingredient combination of α-cyclodextrins and linoleic acid of molar ratios 1:1, 2:1, 3:1 and 4:1 are provided.

Physical mixture of α-cyclodextrin 4:1 linoleic acid. All batches are stored in open dishes at 45° C. in a drying cabinet.

The content of linoleic acid in the physical mixture and the active ingredient combinations was determined by means of NMR.

FIG. 1 shows the linoleic acid content in the stored samples as a function of the storage time.

Example 4

Complexation of Linoleic Acid with β-CD 100 g of $H_2O$ were added to 0.1 mol of β-cyclodextrin, 0.033 mol of linoleic acid were added, and the mixture was homogenized and stirred for 70 h at RT, and for 8 h at 70° C. The active ingredient combination is dispersed in water, filtered, washed with water and dried at 40° C. under reduced pressure.

Example 5

Complexation of Linoleic Acid with γ-CD 100 g $H_2O$ were added to 0.1 mol of γ-cyclodextrin, 0.033 mol of linoleic acid were added, and the mixture was homogenized and stirred for 70 h at RT, and for 8 h at 70° C. The active ingredient combination is dispersed in water, filtered, washed with water and dried at 40° C. under reduced pressure.

Example 6

Preparation of Cosmetic Formulations with an Active Ingredient Combination of α-Cyclodextrin with Linoleic Acid a.) Preparation of a sunscreen cream with an active ingredient combination of α-cyclodextrin with linoleic acid Mix components A and heat to 60° C., add B to A, homogenize, disperse component C for 15 min at 60° C. and mix into AB.

Composition and proportions by weight:

| Active ingredient | Proportions by weight |
|---|---|
| A | |
| Octyl palmitate | 2.5% |
| Octyl stearate | 3.5% |
| Polyglycerol-2 sesquiisostearate | 2.0% |
| Cyclomethicone, dimethiconol | 3.0% |
| Lauryl dimethicone | 2.0% |
| Octyl dimethicone ethoxy glycoside, cyclomethicone | 12.0% |
| B | |
| Titanium dioxide | 5.0% |
| Polymethylsilsesquioxane | 1.0% |
| Zinc Oxide | 2.0% |
| C | |
| Glycerol | 2.0% |
| Methylparaben | 0.1% |
| Sodium chloride | 0.4% |
| Water | 59.0% |
| γ-Cyclodextrin-α-tocopherol complex | 1.5% |
| α-Cyclodextrin-linoleic acid complex | 4.0% | b.) Preparation of a W/O body lotion with an active ingredient combination of α-cyclodextrin with linoleic acid Heat components A to 70° C., disperse B after 30 min at room temperature, heat to 70° C. and introduce into A, homogenize thoroughly, cool with stirring to 40° C., add C, stir further until cool.

Composition and proportions by weight:

| Active ingredients | Proportions by weight |
|---|---|
| A | |
| Beeswax | 3.0% |
| Hostacerin | 3.0% |
| BELSIL ® CM 1000 | 5.0% |
| BELSIL ® DM 1plus | 7.0% |
| BELSIL ® PDM 20 | 4.55% |
| BELSIL ® SPG 128 VP | 12.8% |
| B | |
| Sodium chloride | 2.0% |
| Water | 59.4% |
| α-Cyclodextrin-linoleic acid complex | 4.0% |
| C | |
| Kathon | 0.05% | c) Preparation of an aftersun lotion with an active ingredient combination of α-cyclodextrin with linoleic acid Heat components A and B to 75° C. Disperse component D for 30 min at room temperature, introduce into B, add A with stirring to the mixture of component B and D. After 5 min, add C and cool to 40° C. Add E and cool with stirring to room temperature.

Composition and proportions by weight:

| Active ingredients | Proportions by weight |
|---|---|
| A | |
| Cetyl alcohol | 1.5% |
| Mineral oil | 5.0% |
| Stearic acid | 5.0% |
| B | |
| Allantoin | 0.5% |
| Propylene glycol | 3.0% |
| Water | 45.0% |
| C | |
| Cyclomethicone, dimethicone | 15.0% |
| Phenyltrimethicone | 2.0% |
| D | |
| α-Cyclodextrin-linoleic acid Complex | 2.0% |
| γ-Cyclodextrin-retinol complex | 0.4% |
| Water | 20.0% |
| E | |
| Phenoxyethanol, methylparaben, butylparaben, ethylparaben, propylparaben, | 0.3% |
| Perfume | 0.3% | d) Preparation of an O/W body lotion with an active ingredient combination of α-cyclodextrin with linoleic acid Disperse component A for 30 min at room temperature, heat to 75° C., incorporate B, heat C to 70° C. and slowly stir into AB, then stir in D and cool to room temperature.

Composition and proportions by weight:

| Active ingredients | Proportions by weight |
|---|---|
| A | |
| Carbopol | 0.1.% |
| Water | 80.0% |
| Glycerol | 3.0% |
| α-cyclodextrin-linoleic acid complex | 4.4% |
| B | |
| Triethanolamine | 0.9% |
| C | |
| Stearic Acid | 0.8% |
| Isopropyl myristate | 3.0% |
| Nexbase | 2.0% |
| Arlacel 165 | 1.5% |
| Cetyl alcohol | 1.0% |
| D | |
| BELSIL ® | 3.0% |
| BHT | 0.3% | e.) Preparation of an O/W face cream with an active ingredient combination of α-cyclodextrin with linoleic acid Heat components A+B separately to about 65° C. Disperse phase B for about 10 min, initially introduce, and add phase A with stirring, homogenize.

Composition and proportions by weight:

| Active ingredients | Proportions by weight |
|---|---|
| A | |
| Stearyl glucoside | 3% |
| Glyceryl stearate | 2% |
| Stearyl alcohol | 1% |
| Decyl cocoate | 10% |
| Cetearyl ethylhexanoate | 9% |
| B | |
| Glycerol | 3% |
| Water | 62% |
| α-Cyclodextrin-linoleic acid complex | 9% |
| γ-Cyclodextrin-retinol complex | 1% | f.) Preparation of an O/W moisturizing cream with an active ingredient combination of α-cyclodextrin with linoleic acid Heat components A+B separately to 65° C., disperse phase B for about 10 min, initially introduce, and add phase A with stirring, then phase C. Homogenize the resulting cream formulation.

Composition and proportions by weight:

| Active ingredients | Proportions by weight |
|---|---|
| A | |
| Stearyl glucoside | 3.0% |
| Glyceryl stearate | 2.1% |
| Stearyl alcohol | 0.9% |
| Ethylhexyl stearate | 10.0% |
| Caprylic/capric triglyceride | 10.0% |
| Avocado oil | 3.7% |
| B | |
| Glycerol | 3.0% |
| Water | 59.0% |
| α-Cyclodextrin-linoleic acid complex | 6.0% |
| C | |
| Sodium lactate, urea, lactic acid | 2.0% |
| Tocopheryl acetate | 0.3% | g.) Preparation of a liquid make-up containing active ingredient combination of α-cyclodextrin with linoleic acid Heat A to 75° C., incorporate B into A using Turrax, ensure good pigment distribution, disperse C for about 20 min at 50° C., emulsify into AB using Turrax, cool with stirring to 40° C., stir in D, cool to RT, homogenize until cold using Turrax.

Composition and proportions by weight:

| Active ingredients | Proportions by weight |
|---|---|
| A | |
| White beeswax | 2.70% |
| Polyglyceryl-2 sesquiisostearate | 2.40% |
| Dimethicone | 10.00% |
| Dimethicone | 2.50% |
| Octyl dimethicone ethoxy glucoside, cyclomethicone | 11.00% |
| Trimethyl siloxysilicate | 1.50% |
| B | |
| Iron oxide | 1.45% |
| Talc | 5.00% |
| Titanium dioxide; | 7.00% |
| C | |
| Sodium chloride | 2.00% |
| Water | 50.00% |
| γ-Cyclodextrin-α-tocopherol complex | 1.70% |
| α-Cyclodextrin-linoleic acid complex | 2.40% |
| D | |
| Methylchloroisothiazolinone | 0.05% |
| Perfume | 0.30% | h.) Preparation of a body emulsion containing active ingredient combination of α-cyclodextrin with linoleic acid The raw materials A are initially introduced into a beaker, heated to 65° C., the raw materials B are dispersed in a stirrable vessel at 50° C. for 20 min. Both mixtures are emulsified at 65° C. using a high-speed paddle stirrer and left to cool with further stirring to 40° C. and homogenized using Ultra-Turrax (max. 500 rpm). The air dissolved in the cream is removed by carefully applying a water-jet vacuum.

| Active ingredients | Proportions by weight |
|---|---|
| A | |
| Glyceryl monomyristate | 1.4% |
| Stearic acid | 1.2% |

-continued

| Active ingredients | Proportions by weight |
| --- | --- |
| Cetyl alcohol | 0.5% |
| Isopropyl palmitate | 5.0% |
| B | |
| Water, dist. | 87.5% |
| Methylparaben | 1.0% |
| α-Cyclodextrin-linoleic acid complex | 3.4% |

The Trademark BELSIL® is used for polyorganosiloxanes for cosmetical purposes. The names for the active ingredients of the Trademarks listed above in the application are as follows:

BELSIL® is for Silicone Polyglucoside.

BELSIL® CM 1000 is for mixture of Cyclopentasiloxane and Dimethiconol.

BELSIL® DM 1 Plus is for Dimethicone.

BELSIL® PDM 20 is for Phenyl Trimethicone.

BELSIL® SPG 128 is for a mixture of Caprylyl Dimethicone Ethoxy Glucoside and Cyclopentasiloxane.

ARLACEL® 165 is for a mixture of Glyceryl Stearate and PEG-100 Stearate, PEG 100 Stearate is made by combining natural oils with stearic acid to form a water-soluble ester. PEG stands for polyethylene glycol.

HOSTACERIN® is for Polyglyceryl-2-sesqui-isostearate.

Accordingly, while a few embodiments of the present invention have been shown and described, it is to be understood that many changes and modifications may be made thereunto without departing from the spirit and scope of the invention as defined in the appended claims.

What is claimed is:

1. A cosmetic or dermatological preparation or formulation comprising:
   vitamin F, wherein the vitamin F is an essential fatty acid consisting of an omega-6 polyunsaturated fatty acid and is present in the form of a complex with alpha-cyclodextrin, and
   wherein the essential fatty acid and alpha-cyclodextrin are present in the complex in a ratio selected from the group consisting of 3 mol of alpha-cyclodextrin:1 mol of said essential fatty acid, 4 mol of alpha-cyclodextrin:1 mol of said essential fatty acid, and a mixture of these complexes.

2. A process for preparing a preparation as claimed in claim 1, comprising
   dispersing a complex of vitamin F consisting of an omega-6 polyunsaturated fatty acid and alpha-cyclodextrin in water to form a dispersion; and
   then mixing the dispersion into a lipophilic part of an emulsion.

3. A cosmetic or dermatological preparation or formulation comprising:
   linoleic acid or alpha linoleic acid present in the form of a complex with alpha-cyclodextrin,
   wherein the linoleic acid or alpha linoleic acid and alpha-cyclodextrin are present in the complex in a ratio selected from the group consisting of 3 mol of alpha-cyclodextrin:1 mol of linoleic acid or alpha linolenic acid, 4 mol of alpha-cyclodextrin:1 mol of linoleic acid or alpha linoleic acid, and a mixture of these complexes.

4. A process for preparing a preparation as claimed in claim 3, comprising:
   dispersing a complex of linoleic acid or alpha-linoleic acid, and alpha-cyclodextrin in water to form a dispersion; and
   then mixing the dispersion into a lipophilic part of an emulsion.

5. The cosmetic or dermatological preparation or formulation according to claim 3, wherein the complex comprises a complex of linoleic acid and cyclodextrin in a ratio selected from the group consisting of 3 mol of alpha-cyclodextrin:1 mol of linoleic acid, 4 mol of alpha-cyclodextrin:1 mol of linoleic acid, and a mixture of these complexes.

* * * * *

UNITED STATES PATENT AND TRADEMARK OFFICE
CERTIFICATE OF CORRECTION

PATENT NO.        : 7,667,057 B2                                          Page 1 of 1
APPLICATION NO.   : 10/712703
DATED             : February 23, 2010
INVENTOR(S)       : Regiert et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 867 days.

Signed and Sealed this

Seventh Day of December, 2010

David J. Kappos
*Director of the United States Patent and Trademark Office*